(12) United States Patent
Schelberger et al.

(10) Patent No.: US 8,530,380 B2
(45) Date of Patent: Sep. 10, 2013

(54) FUNGICIDAL MIXTURES BASED ON AMIDE COMPOUNDS AND MORPHOLINE OR PIPERIDINE DERIVATIVES

(75) Inventors: Klaus Schelberger, Gönnheim (DE); Maria Scherer, Landau (DE); Karl Eicken, Wachenheim (DE); Manfred Hampel, Neustadt (DE); Eberhard Ammermann, Heppenheim (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 2248 days.

(21) Appl. No.: 11/322,211

(22) Filed: Dec. 30, 2005

(65) Prior Publication Data

US 2008/0103144 A1    May 1, 2008

Related U.S. Application Data

(62) Division of application No. 10/183,618, filed on Jun. 28, 2002, now Pat. No. 7,109,221, which is a division of application No. 09/581,834, filed as application No. PCT/EP98/08230 on Dec. 15, 1998, now Pat. No. 6,436,934.

(30) Foreign Application Priority Data

Dec. 18, 1997 (DE) .................... 197 56 382

(51) Int. Cl.
*A01N 25/26* (2006.01)
*A01N 43/40* (2006.01)
(52) U.S. Cl.
USPC .......................................... 504/100; 504/130
(58) Field of Classification Search
USPC ........................................................ 424/405
See application file for complete search history.

(56) References Cited

U.S. PATENT DOCUMENTS

| | | | |
|---|---|---|---|
| 4,927,823 A | 5/1990 | Gisi | 514/237 |
| 5,330,984 A | 7/1994 | Küng et al. | 514/239 |
| 5,330,995 A | 7/1994 | Eicken et al. | 514/355 |
| 5,424,317 A | 6/1995 | Küng et al. | 514/317 |
| 5,438,070 A | 8/1995 | Eicken et al. | 514/403 |
| 5,491,165 A | 2/1996 | Dehne et al. | 514/479 |
| 5,532,262 A | 7/1996 | Brandes et al. | 514/388 |
| 6,130,224 A | 10/2000 | Eicken et al. | 514/259 |
| 6,143,745 A * | 11/2000 | Eicken et al. | 514/247 |
| 6,169,056 B1 | 1/2001 | Bayer et al. | 504/118 |
| 6,172,063 B1 | 1/2001 | Müller et al. | 514/237 |
| 6,262,091 B1 | 7/2001 | Wagner et al. | 514/355 |
| 6,436,934 B1 * | 8/2002 | Schelberger et al. | 514/237.5 |
| 6,638,961 B2 * | 10/2003 | Latorse | 514/398 |
| 7,109,221 B2 * | 9/2006 | Schelberger et al. | 514/355 |

FOREIGN PATENT DOCUMENTS

WO    WO 96/03044    * 2/1996

* cited by examiner

*Primary Examiner* — Alton Pryor
(74) *Attorney, Agent, or Firm* — Novak Druce Connolly Bove + Quigg LLP

(57) ABSTRACT

Fungicidal mixtures comprise as active components
a) an amide compound of the formula I $$A\text{-}CO\text{-}NR^1R^2 \qquad \qquad I$$

in which A, $R^1$ and $R^2$ are as defined in the description, and
b) dimethomorph or flumetover, and/or
c) a valinamide of the formula III $$R^{13}O-\underset{\underset{O}{\|}}{C}-NH-\underset{\underset{CH_3-CH-CH_3}{|}}{CH}-\underset{\underset{O}{\|}}{C}-NH-\underset{\underset{CH_3}{|}}{CH}-R^{14} \qquad (III)$$

in which
$R^{13}$ is $C_3$-$C_4$-alkyl and
$R^{14}$ is naphthyl or phenyl, where the phenyl radical is substituted in the 4-position by a halogen atom, a $C_1$-$C_4$-alkyl or $C_1$-$C_4$-alkoxy group, and/or
d) benalaxyl, ofurace, metalaxyl, furalaxyl or oxydixyl, and/or
e) 1-(2-cyano-2-methoxyiminoacetyl)-3-ethylurea
in a synergistically effective amount.

12 Claims, No Drawings

FUNGICIDAL MIXTURES BASED ON AMIDE COMPOUNDS AND MORPHOLINE OR PIPERIDINE DERIVATIVES

This is a Divisional application of application Ser. No. 10/183,618, filed on Jun. 28, 2002 (allowed), the entire disclosure of which is herewith incorporated by reference, which is a Divisional application of application Ser. No. 09/581,834, filed on Jun. 19, 2000, now U.S. Pat. No. 6,436,934, the entire disclosure of which is herewith incorporated by reference.

The present invention relates to fungicidal mixtures for controlling harmful fungi and also to methods for controlling harmful fungi using such mixtures.

WO 97/08952 describes mixtures of amide compounds of the formula I

A-CO—NR$^1$R$^2$     (I)

in which

A is an aryl group or an aromatic or non-aromatic, 5- or 6-membered heterocycle which has from 1 to 3 heteroatoms selected from O, N and S;

where the aryl group or the heterocycle may or may not have 1, 2 or 3 substituents which are selected, independently of one another, from alkyl, halogen, CHF$_2$, CF$_3$, alkoxy, haloalkoxy, alkylthio, alkylsulfynyl and alkylsulfonyl;

R$^1$ is a hydrogen atom;

R$^2$ is a phenyl or cycloalkyl group which may or may not have 1, 2 or 3 substituents which are selected from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may or may not be condensed with a saturated 5-membered ring which may or may not be substituted by one or more alkyl groups and/or may have a heteroatom selected from O and S, and the active ingredient fenazaquin which is known as an acaricide.

These mixtures are described as being particularly effective against *Botrytis*.

It is an object of the present invention to provide further particularly effective mixtures for controlling harmful fungi and in particular for certain indications.

We have found, surprisingly, that this object is achieved by a mixture which comprises as active ingredients amide compounds of the formula I defined above and as further fungicidally active component b) a carboxamide II selected from the group of the compounds IIa and IIb

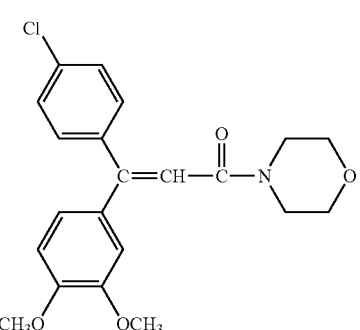
(IIa)

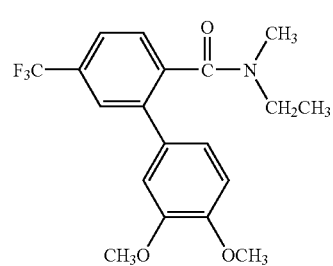
(IIb)

and/or c) a valinamide of the formula III

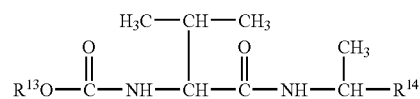
(III)

in which

R$^{13}$ is C$_3$-C$_4$-alkyl and

R$^{14}$ is naphthyl or phenyl, where the phenyl radical in the 4-position is substituted by a halogen atom, a C$_1$-C$_4$-alkyl or a C$_1$-C$_4$-alkoxy group, and/or d) at least one active ingredient of the formulae IV.1 to IV.5,

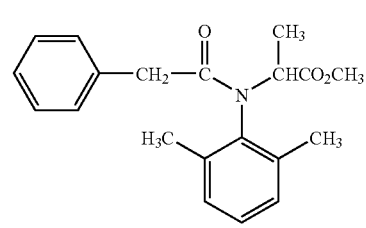
(IV.1)

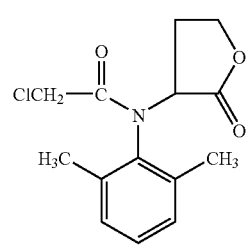
(IV.2.)

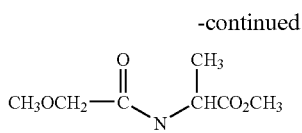
(IV.3)

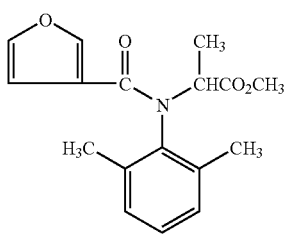
(IV.4)

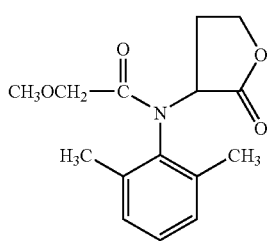
(IV.5)

and/or e) 1-(2-cyano-2-methoxyiminoacetyl)-3-ethylurea (V)

$$H_3CCH_2-NHCONH-C(CN)=NOCH_3 \qquad V$$

in a synergistically effective amount.

The mixtures according to the invention have synergistic action and are therefore particularly suitable for controlling harmful fungi and in particular downy mildew fungi in vegetables and grapevines.

In the context of the present invention, halogen is fluorine, chlorine, bromine and iodine and is in particular fluorine, chlorine and bromine.

The term "alkyl" includes straight-chain and branched alkyl groups. These are preferably straight-chain or branched $C_1$-$C_{12}$-alkyl and in particular $C_1$-$C_6$-alkyl groups. Examples of alkyl groups are alkyl such as, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular by fluorine and chlorine. Preferably, there are from 1 to 3 halogen atoms present, and the difluoromethyl or the trifluoromethyl group is particularly preferred.

The above statements for the alkyl group and the haloalkyl group apply in a corresponding manner to the alkyl and haloalkyl groups in alkoxy, haloalkoxy, alkylthio, haloalkylthio, alkylsulfynyl and alkylsulfonyl.

The alkenyl group includes straight-chain and branched alkenyl groups. These are preferably straight-chain or branched $C_3$-$C_{12}$-alkenyl groups and in particular $C_3$-$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group may be partially or fully halogenated by one or more halogen atoms, in particular by fluorine or chlorine. This group preferably has from 1 to 3 halogen atoms.

The alkynyl group includes straight-chain and branched alkynyl groups. These are preferably straight-chain and branched $C_3$-$C_{12}$-alkynyl groups and in particular $C_3$-$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

The above statements for the alkenyl group and its halogen substituents and for the alkynyl group apply in a corresponding manner to alkenyloxy and alkynyloxy.

The cycloalkyl group is preferably a $C_3$-$C_6$-cycloalkyl group, such as cyclopropyl, cyclobutyl, cyclopentyl or cyclohexyl.

If the cycloalkyl group is substituted, it preferably has from 1 to 3 $C_1$-$C_4$-alkyl radicals as substituents.

Cycloalkenyl is preferably a $C_4$-$C_6$-cycloalkenyl group, such as cyclobutenyl, cyclopentenyl or cyclohexenyl. If the cycloalkenyl group is substituted, it preferably has from 1 to 3 $C_1$-$C_4$-alkyl radicals as substituents.

A cycloalkoxy group is preferably a $C_5$-$C_6$-cycloalkoxy group, such as cyclopentyloxy or cyclohexyloxy. If the cycloalkoxy group is substituted, it preferably has from 1 to 3 $C_1$-$C_4$-alkyl radicals as substituents.

The cycloalkenyloxy group is preferably a $C_5$-$C_6$-cycloalkenyloxy group, such as cyclopentyloxy or cyclohexyloxy. If the cycloalkenyloxy group is substituted, it preferably has from 1 to 3 $C_1$-$C_4$-alkyl radicals as substituents.

Aryl is preferably phenyl.

If A is a phenyl group, this may have one, two or three of the abovementioned substituents in any position. These substituents are preferably selected, independently of one another, from alkyl, difluoromethyl, trifluoromethyl and halogen, in particular chlorine, bromine and iodine. Particularly preferably, the phenyl group has a substituent in the 2-position.

If A is a 5-membered heterocycle, it is in particular a furyl, thiazolyl, pyrazolyl, imidazolyl, oxazolyl, thienyl, triazolyl or thiadiazolyl radical or the corresponding dihydro or tetrahydro derivatives thereof. Preference is given to a thiazolyl or pyrazolyl radical.

If A is a 6-membered heterocycle, it is in particular a pyridyl radical or a radical of the formula:

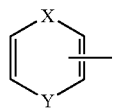

in which one of the radicals X and Y is O, S or $NR^{12}$, where $R^{12}$ is H or alkyl, and the other of the radicals X and Y is $CH_2$, S, SO, $SO_2$ or $NR^{12}$. The dotted line means that a double bond may or may not be present.

The 6-membered aromatic heterocycle is particularly preferably a pyridyl radical, in particular a 3-pyridyl radical, or a radical of the formula

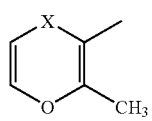
(A3)

in which X is $CH_2$, S, SO or $SO_2$.

The abovementioned heterocyclic radicals may or may not have 1, 2 or 3 of the abovementioned substituents, where these substituents are preferably selected, independently of one another, from alkyl, halogen, difluoromethyl or trifluoromethyl.

A is particularly preferably a radical of the formulae:

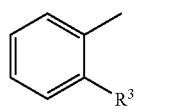
(A1)

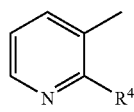
(A2)

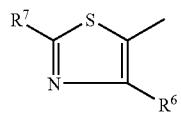
(A5)

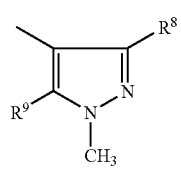
(A7)

in which $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in the formula I is preferably a hydrogen atom.

The radical $R^2$ in the formula I is preferably a phenyl radical. $R^2$ preferably has at least one substituent which is particularly preferably in the 2-position. The substituent (or the substituents) is (are) preferably selected from the group consisting of alkyl, cycloalkyl, cycloalkenyl, halogen and phenyl.

The substituents of the radical $R^2$ may in turn be substituted again. The aliphatic or cycloaliphatic substituents may be partially or fully halogenated, in particular fluorinated or chlorinated. They preferably have 1, 2 or 3 fluorine or chlorine atoms. If the substituent of the radical $R^2$ is a phenyl group, this group may preferably be substituted by from 1 to 3 halogen atoms, in particular chlorine atoms, and/or by a radical which is preferably selected from alkyl and alkoxy. Particularly preferably, the phenyl group is substituted with a halogen atom in the p-position, i.e. the particularly preferred substituent of the radical $R^2$ is a p-halogen-substituted phenyl radical. The radical $R^2$ may also be condensed with a saturated 5-membered ring, where this ring for its part may have from 1 to 3 alkyl substituents.

$R^2$ is in this case, for example, indanyl, thiaindanyl and oxaindanyl. Preference is given to indanyl and 2-oxaindanyl which are attached to the nitrogen atom in particular via the 4-position.

According to a preferred embodiment, the composition according to the invention comprises as amide compound a compound of the formula I in which A is as defined below: phenyl, pyridyl, dihydropyranyl, dihydrooxathiynyl, dihydrooxathiynyloxide, dihydrooxathiynyldioxide, furyl, thiazolyl, pyrazolyl or oxazolyl, where these groups may have 1, 2 or 3 substituents which are selected, independently of one another, from alkyl, halogen, difluoromethyl and trifluoromethyl.

According to a further preferred embodiment, A is: pyridin-3-yl, which may or may not be substituted in the 2-position by halogen, methyl, difluoromethyl, trifluoromethyl, methoxy, methylthio, methylsulfynyl or methylsulfonyl;

phenyl, which may or may not be substituted in the 2-position by methyl, trifluoromethyl, chlorine, bromine or iodine;

2-methyl-5,6-dihydropyran-3-yl;

2-methyl-5,6-dihydro-1,4-oxathiyn-3-yl or the 4-oxide or 4,4-dioxide thereof;

2-methylfuran-3-yl, which may or may not be substituted in the 4- and/or 5-position by methyl;

thiazol-5-yl, which may or may not be substituted in the 2- and/or 4-position by methyl, chlorine, difluoromethyl or trifluoromethyl;

thiazol-4-yl, which may or may not be substituted in the 2- and/or 5-position by methyl, chlorine, difluoromethyl or trifluoromethyl;

1-methylpyrazol-4-yl, which may or may not be substituted in the 3- and/or 5-position by methyl, chlorine, difluoromethyl or trifluoromethyl; or oxazol-5-yl, which may or may not be substituted in the 2- and/or 4-position by methyl or chlorine.

According to a further preferred embodiment, the compositions according to the invention comprise as amide compound a compound of the formula I in which $R^2$ is a phenyl group which may or may not be substituted by 1, 2 or 3 of the abovementioned substituents.

According to a further preferred embodiment, the compositions according to the invention comprise as amide compound a compound of the formula I in which $R^2$ is a phenyl group which has one of the following substituents in the 2-position:

$C_3$-$C_6$-alkyl, $C_5$-$C_6$-cycloalkenyl, $C_5$-$C_6$-cycloalkyloxy, cycloalkenyloxy, where these groups may be substituted by 1, 2 or 3 $C_1$-$C_4$-alkyl groups, phenyl, which is substituted by from 1 to 5 halogen atoms and/or from 1 to 3 groups which are selected, independently of one another, from $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, indanyl or oxaindanyl which may or may not be substituted by 1, 2 or 3 $C_1$-$C_4$-alkyl groups.

According to a further preferred embodiment, the compositions according to the invention comprise as amide compound a compound of the formula Ia,

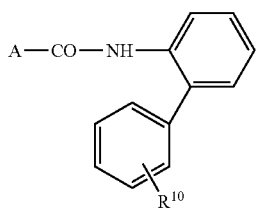
(Ia)

in which
A is

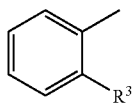
(A1)

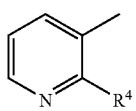
(A2)

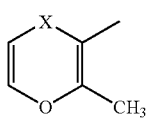
(A3)

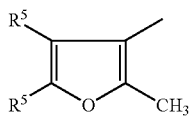
(A4)

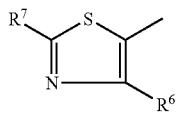
(A5)

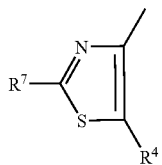
(A6)

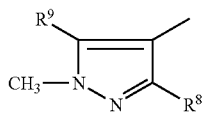
(A7)

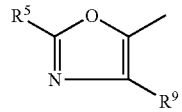
(A8)

X is methylene, sulfur, sulfynyl or sulfonyl ($SO_2$),
$R^3$ is methyl, difluoromethyl, trifluoromethyl, chlorine, bromine or iodine,
$R^4$ is trifluoromethyl or chlorine,
$R^5$ is hydrogen or methyl,
$R^6$ is methyl, difluoromethyl, trifluoromethyl or chlorine,
$R^7$ is hydrogen, methyl or chlorine,
$R^8$ is methyl, difluoromethyl or trifluoromethyl,
$R^9$ is hydrogen, methyl, difluoromethyl, trifluoromethyl or chlorine,
$R^{10}$ is $C_1$-$C_4$-alkyl, $C_1$-$C_4$-alkoxy, $C_1$-$C_4$-alkylthio or halogen.

According to a particularly preferred embodiment, the compositions comprise as amide compound a compound of the formula Ib

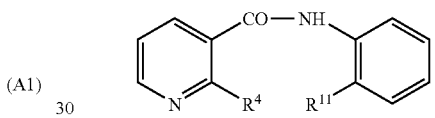
(Ib)

in which
$R^4$ is halogen and
$R^{11}$ is phenyl which is substituted by halogen.

Particularly preferred mixtures according to the invention comprise as component I compounds of the formulae

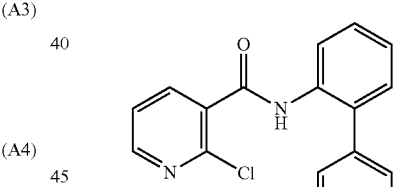

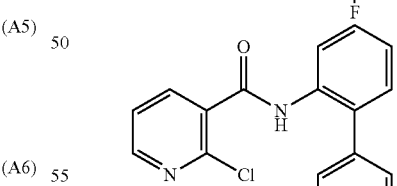

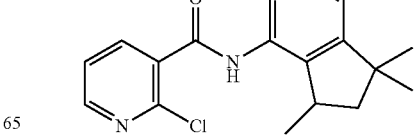

Useful amide compounds of the formula I are mentioned in EP-A-545 099 and 589 301 which are incorporated herein in their entirety by reference.

The preparation of the amide compounds of the formula I is known, for example, from EP-A-545 099 or 589 301 or can be carried out by similar processes.

Also known are the carboxamides II [IIa: common name: dimethomorph, EP-A 120 321; IIb: proposed common name: flumetover, AGROW No. 243, 22 (1995)], their preparation and their action against harmful fungi.

The compounds of the formula III are also known per se. A first preferred group of valinamide derivatives are compounds of the formula III'

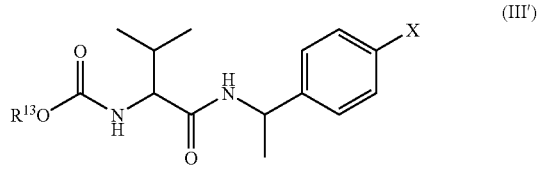

in which $R^{13}$ is as defined above and X is halogen, $C_1$-$C_4$-alkyl or $C_1$-$C_4$-alkoxy. Compounds of this type and their preparation are described, for example, in EP-A-0 610 764 and EP-A-0 398 072, which are expressly incorporated herein by way of reference.

A further preferred group of valinamide derivatives are compounds of the formula III"

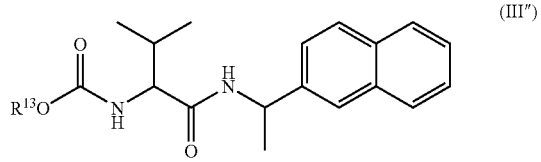

in which $R^{13}$ is as defined above. Compounds of this type and their preparation are described, for example, in DE-A-43 21 897 and WO-A-96/07638, which are expressly incorporated herein by way of reference.

Preference is given to compounds of the formula III in which $R^{13}$ is isopropyl, sec-butyl and tert-butyl.

Likewise, preference is given to compounds of the formula III in which $R^{14}$ is a-naphthyl, β-naphthyl and phenyl, the phenyl radical being substituted in the 4-position by chlorine, bromine, $C_1$-$C_4$-alkyl or $C_1$-$C_4$-alkoxy.

Particular preference is given to compounds of the formula III in which $R^{14}$ is SS-naphthyl, 4-chlorophenyl, 4-methylphenyl and 4-methoxyphenyl.

Preferred examples of valinamides which can be used according to the invention are summarized in Table 2 below.

TABLE 2

| No. | $R^{13}$ | $R^{14}$ |
|---|---|---|
| III.1 | isopropyl | β-naphthyl |
| III.2 | isopropyl | 4-chlorophenyl |
| III.3 | isopropyl | 4-methylphenyl |
| III.4 | isopropyl | 4-methoxyphenyl |
| III.5 | sec-butyl | β-naphthyl |
| III.6 | sec-butyl | 4-chlorophenyl |
| III.7 | sec-butyl | 4-methylphenyl |
| III.8 | sec-butyl | 4-methoxyphenyl |
| III.9 | tert-butyl | β-naphthyl |

TABLE 2-continued

| No. | $R^{13}$ | $R^{14}$ |
|---|---|---|
| III.10 | tert-butyl | 4-chlorophenyl |
| III.11 | tert-butyl | 4-methylphenyl |
| III.12 | tert-butyl | 4-methoxyphenyl |

Particular preference is given to the compounds 111.2 and III.9.

From the structural formula for the compounds of the formula III it is evident that these compounds have two asymmetrically substituted carbon atoms. The compounds can therefore be used for the mixture according to the invention either as mixtures of different isomers or as pure isomers.

In a further preferred embodiment, compounds of the formula III are used in which the amino acid moiety is formed by alkoxycarbonyl-L-valine (S configuration) and the phenethylamine moiety or the naphthylethylamine moiety has the R configuration. Such compounds can be represented by the formula IIIa

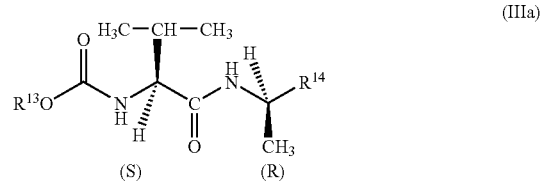

in which $R^{13}$ and $R^{14}$ are as defined for the compounds of the formula II.

The preparation of the preferred isomers of the formula IIIa is carried out similarly to the methods described in the earlier German patent application DE-A-195 31 814. The disclosure of this application is expressly incorporated herein by way of reference.

The isomerically pure compounds of the formula IIIa can be prepared in a manner known per se starting from the appropriate, L-valine-based carbamoylcarboxylic acids VI. The compounds IIIa are obtained, for example, by the process described below in which a carbamoylcarboxylic acid VI is reacted with an amine VII (the literature references "Houben-Weyl" refer to: Houben-Weyl, Methoden der Organischen Chemie, 4th edition, Thieme Verlag, Stuttgart):

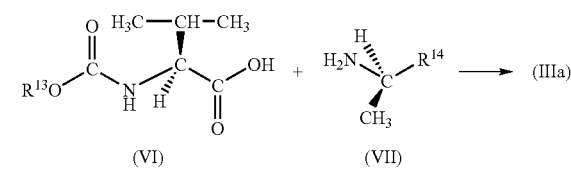

The carbamoylcarboxylic acids VI are known or can be prepared by known methods, in particular starting from the amino acid L-valine (cf. "Houben-Weyl", volume 15/1, pp. 46-305, in particular pp. 117-125).

The amines VII are also known or can be easily obtained (cf. Organikum, VEB Deutscher Verlag der Wissenschaften, 15th edition, Berlin, 1977, p. 610 ff.; "Houben-Weyl", volume 15/1, pp. 648-665; Indian J. Chem. 10, pp. 366 (1972); J. Am. Chem. Soc. 58, pp. 1808-1811 (1936)).

From racemates of the amines VII, the R isomer can be isolated in a manner known per se, for example by fractional crystallization using optically active tartaric acid or, preferably, by enzyme-catalyzed esterification and subsequent hydrolysis (cf., for example, WO-A-95/08636).

This process is preferably carried out by initially converting the carbamoylcarboxylic acids VI into carboxyl-ativaited derivatives, in particular into acyl cyanides or anhydrides, (cf. Tetrahedron Letters, volume 18, pp. 1595-1598 (1973), or "Houben-Weyl", volume 15/1, pp. 28-32). These derivatives are then reacted with the amines VII in the presence of bases.

Suitable for preparing the carboxyl-activated acyl cyanides is, for example, the reaction of the carbamoylcarboxylic acids V with diethyl cyanophosphonate, in particular in an inert solvent, such as tetrahydrofuran or toluene.

The preparation of the carboxyl-activated anhydrides is preferably carried out by reacting the carbamoylcarboxylic acid V with chloroformates, such as isobutyl chloroformate, in the presence of bases and, if appropriate, in an inert solvent, such as toluene or tetrahydrofuran.

The reaction of the amines VII with the carboxyl-activated carbamoylcarboxylic acids VI is preferably carried out in a solvent such as dichloromethane, tetrahydrofuran or toluene.

The amines VII may also serve as bases, in which case they are usually recovered from the crude product.

In a preferred embodiment of this process step, the carbamoylcarboxylic acid VI, the amine VII, the reagent which is suitable for generating the carboxyl-activated derivative of the carbamoylcarboxylic acid VI and the base are reacted in a one-pot process, if appropriate in an inert solvent, and the crude product is subsequently worked-up in a manner known per se to isolate the carbamoylcarboxamide IIIa.

The compound IV.1 is commercially available under the common name benalaxyl or the trade name Galben™

The compound IV.2 is commercially available under the common name ofurace or the trade name Celtan™ P in the form of mixtures with cymoxanil and folpet.

The compound IV.3 is commercially available under the common name metalaxyl or the trade name Ridomil™

The compound IV.4 is commercially available under the common name furalaxyl or the trade name Fongaride™

The compound of the formula IV.5 is commercially available under the common name oxadixyl and under the trade name Sandofan™C in mixtures with copper salts.

Processes for preparing the compounds of the formula IV are known per se to the person skilled in the art, and there is therefore no need to mention them here in any detail.

The compound V (U.S. Pat. No. 3,957,847; common name: cymoxanil), its preparation and its action against harmful fungi are also known.

To unfold the synergistic activity, even a small amount of amide compound of the formula I is sufficient. Preference is given to employing amide compound and compounds II and/or the compounds III to V in a weight ratio in the range of from 20:1 to 1:20, in particular 10:1 to 1:10.

When preparing the mixtures, it is preferred to employ the pure active ingredients I and II and/or III to V, to which further active ingredients against harmful fungi or other pests, such as insects, arachnids or nematodes, or else herbicidal or growth-regulating active ingredients or fertilizers can be admixed.

The mixtures of the compounds I and II and/or III to V, or the compounds I and II and/or III to V used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

The mixtures according to the invention may particularly preferably be employed for controlling powdery mildew fungi in vegetables and grapevines.

The compounds I and II and/or III to V can be applied simultaneously, either together or separately, or in succession, the sequence, in the case of separate application, generally not having any effect on the result of the control measures.

Depending on the kind of effect desired, the application rates of the mixtures according to the invention are, in particular in agricultural crop areas, from 0.01 to 8 kg/ha, preferably from 0.1 to 5 kg/ha, in particular from 0.5 to 3.0 kg/ha.

The application rates of the compounds I are from 0.01 to 2.5 kg/ha, preferably from 0.05 to 2.5 kg/ha, in particular from 0.1 to 1.0 kg/ha.

Correspondingly, in the case of the compounds II and/or III to V, the application rates are from 0.01 to 10 kg/ha, preferably from 0.05 to 5 kg/ha, in particular from 0.05 to 2.0 kg/ha.

For seed treatment, the application rates of the mixture are generally from 0.001 to 250 g/kg of seed, preferably from 0.01 to 100 g/kg, in particular from 0.01 to 50 g/kg.

If phytopathogenic harmful fungi are to be controlled, the separate or joint application of the compounds I and II and/or III to V or of the mixtures of the compounds I and II and/or III to V is effected by spraying or dusting the seeds, the plants or the soils before or after sowing of the plants, or before or after plant emergence.

The fungicidal synergistic mixtures according to the invention, or the compounds I and II and/or III to V, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, eg. by extending the active ingredient with solvents and/or carriers, if desired using emulsifiers and dispersants, it being possible also to use other organic solvents as auxiliary solvents if water is used as the diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. finely divided silica, silicates); emulsifiers such as nonionic and anionic emulsifiers (eg. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalene-sulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders, materials for broadcasting and dusts can be prepared by mixing or jointly grinding the compounds I or II and/or III to V, or the mixture of the compounds I and II and/or III to V, with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin, such as cereal meal, tree bark meal, wood meal and nut-shell meal, cellulose powders or other solid carriers.

The formulations generally comprise from 0.1 to 95% by weight, preferably from 0.5 to 90% by weight, of one of the compounds I or II or of the mixture of the compounds I and II and/or III to V. The active ingredients are employed in a purity of from 90% to 100%, preferably from 95% to 100% (according to NMR spectrum or HPLC).

The compounds I or II and/or III to V, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II and/or III to V in the case of separate application.

Application can be effected before or after infection by the harmful fungi.

Examples of such preparations comprising the active ingredients are:

I. A solution of 90 parts by weight of the active ingredients and 10 parts by weight of N-methylpyrrolidone; this solution is suitable for use in the form of microdrops;

II. A mixture of 20 parts by weight of the active ingredients, 80 parts by weight of xylene, 10 parts by weight of the adduct of 8 to 10 mol of ethylene oxide to 1 mol of oleic acid N-monoethanolamide, 5 parts by weight of the calcium salt of dodecylbenzenesulfonate, 5 parts by weight of the adduct of 40 mol of ethylene oxide to 1 mol of castor oil; a dispersion is obtained by finely distributing the solution in water;

III. An aqueous dispersion of 20 parts by weight of the active ingredients, 40 parts by weight of cyclohexanone, 30 parts by weight of isobutanol, 20 parts by weight of the adduct of 40 mol of ethylene oxide to 1 mol of castor oil;

IV. An aqueous dispersion of 20 parts by weight of the active ingredients, 25 parts by weight of cyclohexanol, 65 parts by weight of a mineral oil fraction of boiling point 210 to 280° C., and 10 parts by weight of the adduct of 40 mol of ethylene oxide to 1 mol of castor oil;

V. A mixture, ground in a hammer mill, of 80 parts by weight of the active ingredients, 3 parts by weight of the sodium salt of diisobutylnaphthalene-1-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. An intimate mixture of 3 parts by weight of the active ingredients and 97 parts by weight of finely divided kaolin; this dust comprises 3% by weight of active ingredient;

VII. An intimate mixture of 30 parts by weight of the active ingredients, 92 parts by weight of pulverulent silica gel and 8 parts by weight of paraffin oil which has been sprayed onto the surface of this silica gel; this formulation imparts good adhesion to the active ingredient;

VIII. A stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion may be diluted further;

IX. A stable oily dispersion of 20 parts by weight of the active ingredients, 2 parts by weight of the calcium salt of dodecylbenzenesulfonate, 8 parts by weight of fatty alcohol polyglycol ether, 20 parts by weight of the sodium salt of a phenolsulfonic acid/urea/formaldehyde condensate and 88 parts by weight of a paraffinic mineral oil.

USE EXAMPLE

The synergistic activity of the mixtures according to the invention can be demonstrated by the following experiments:

The active ingredients, separately or together, are formulated as a 10% emulsion in a mixture of 63% by weight of cyclohexanone and 27% by weight of emulsifier, and diluted with water to the desired concentration.

Evaluation is carried out by determining the infected leaf areas in percent. These percentages are converted into efficacies. The efficacy ($\underline{W}$) is calculated as follows using Abbot's formula:

$$W = (1-a) \cdot 100/\beta$$

a corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients are determined using Colby's formula [R. S. Colby, Weeds 15, 20-22 (1967)] and compared with the observed efficacies.

$$E = x+y-x \cdot y/100 \qquad \text{Colby formula:}$$

E expected efficacy, expressed in % of the untreated control, when using the mixture of the active ingredients A and B at the concentrations a and b x efficacy, expressed in % of the untreated control, when using active ingredient A at a concentration a y efficacy, expressed in % of the untreated control, when using active ingredient B at a concentration b Use Example 1

Activity Against *Phytophthora infestans* on Tomatoes

Leaves of potted plants of the variety "Große Fleischtomate" were sprayed to runoff point with an aqueous suspension which had been prepared from a stock solution comprising 10% of active ingredient, 63% of cyclohexanone and 27% of emulsifier. The next day, the leaves were infected with an aqueous zoospore suspension of *Phytophthora infestans*. The plants were subsequently placed in a chamber saturated with water vapor, at temperatures between 16 and 18° C. After 6 days, the tomato blight on the untreated but infected control plants had developed to such an extent that the infection could be determined visually in %.

The compounds of the formula I employed was the following compound:

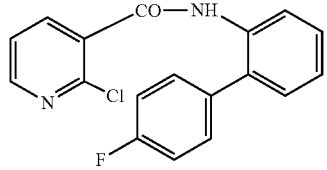

I.1

The results are shown in Tables 1 and 2 below.

TABLE 1

| Ex. | Active ingredient | Concentration of active ingredient in the spray liquor in ppm | Efficacy in % of the untreated control |
|---|---|---|---|
| 1C | Control (untreated) | 0 (100% infection) | 0 |
| 2C | Compound I.1 | 3.1 | 0 |
| 4C | Compound IV.3 | 3.1 | 0 |

TABLE 2

| Ex. | Mixtures according to the invention (content in ppm) | Observed efficacy | Calculated efficacy *) |
|---|---|---|---|
| 5 | 3.1 ppm I.1 + 3.1 ppm IV.3 | 20 | 0 |

The test results show that the observed efficacy in all mixing ratios is higher than the efficacy which had been calculated beforehand using Colby's formula.

We claim:

1. A fungicidal composition comprising as active components
a) an amide compound of the formula Ib

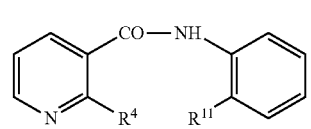

(Ib)

in which
$R^4$ is halogen and
$R^{11}$ is phenyl which is substituted by halogen, and
d) at least one active ingredient of formulae IV.1 to IV.5,

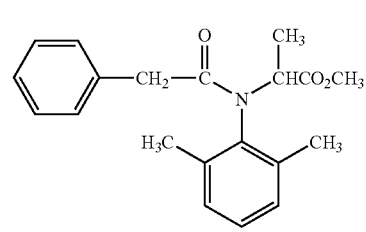

(IV.1)

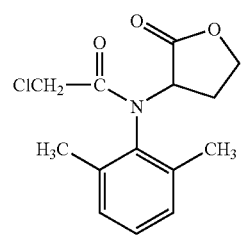

(IV.2)

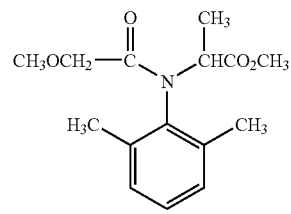

(IV.3)

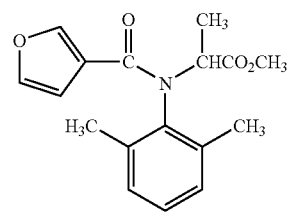

(IV.4)

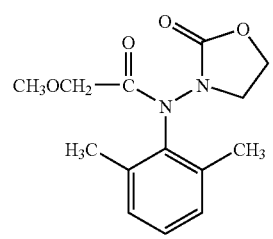

(IV.5)

wherein the active components are present in synergistically effective amounts.

2. The composition defined in claim 1, wherein the amide compound is a compound of formula

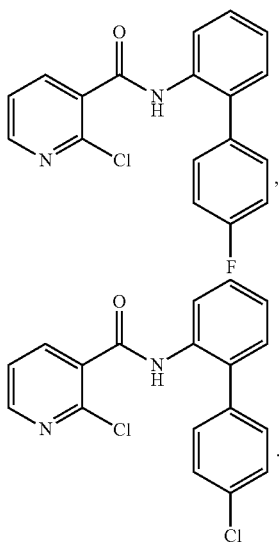

3. The composition defined in claim 1, which is conditioned in two parts, one part comprising the amide compound of formula I in a solid or liquid carrier and the other part comprising one or more active ingredients of formulae IV.1 to IV.5 in a solid or liquid carrier.

4. A method for controlling harmful fungi, which comprises treating the fungi, their habitat, or materials, plants, seeds, soils, areas or spaces to be protected against fungal attack with an effective amount of the composition defined in claim 1, wherein the active components are applied simultaneously, that is either together or separately, or in succession.

5. The composition defined in claim 1, which further comprises 1-(2-cyano-2-methoxyiminoacetyl)-3-ethylurea of formula V

H₃CCH₂—NHCONH—C(CN)=NOCH₃     V.

6. The method of claim 4, wherein the composition further comprises 1-(2-cyano-2-methoxyiminoacetyl)-3-ethylurea of formula V

H₃CCH₂—NHCONH—C(CN)=NOCH₃     V.

7. The composition defined in claim 1, wherein the active components (a) and (d) are present in a weight ratio of from 20:1 to 1:20.

8. The composition defined in claim 7, wherein the active components (a) and (d) are present in a weight ratio of from 10:1 to 1:10.

9. The method of claim 4, wherein the active components (a) and (d) are applied in a weight ratio of from 20:1 to 1:20.

10. The method of claim 9, wherein the active components (a) and (d) are applied in a weight ratio of from 10:1 to 1:10.

11. The method of claim 4, wherein the composition is applied to the fungi, their habitat, or to materials, plants, soils or areas in an amount of from 0.01 to 8.0 kg/ha.

12. The method of claim 4, wherein the composition is applied to seeds in an amount of from 0.001 to 250 g/kg.

* * * * *